United States Patent
Arffa et al.

(10) Patent No.: US 10,340,047 B2
(45) Date of Patent: Jul. 2, 2019

(54) HEALTH TREND IDENTIFICATION

(71) Applicant: International Business Machines Corporation, Armonk, NY (US)

(72) Inventors: Brian Arffa, Franklin, MA (US); Fang Lu, Billerica, MA (US); Yajuan Wang, White Plains, NY (US); Steven I. Ross, S Hamilton, MA (US); Shilpa N. Mahatma, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/846,270

(22) Filed: Dec. 19, 2017

(65) Prior Publication Data
US 2019/0096529 A1   Mar. 28, 2019

Related U.S. Application Data (63) Continuation of application No. 15/715,353, filed on Sep. 26, 2017.

(51) Int. Cl.
*G16H 50/30* (2018.01)
*G16H 15/00* (2018.01)
*G06F 3/0481* (2013.01)
*G06F 3/0484* (2013.01)

(52) U.S. Cl.
CPC ............. *G16H 50/30* (2018.01); *G16H 15/00* (2018.01); *G06F 3/04817* (2013.01); *G06F 3/04842* (2013.01)

(58) Field of Classification Search
CPC ............................... G15H 15/00; G15H 50/30
USPC ......................................................... 705/2–4
See application file for complete search history.

(56) References Cited

U.S. PATENT DOCUMENTS

| | | |
|---|---|---|
| 8,015,030 B2 | 9/2011 | Brown |
| 2011/0184247 A1 | 7/2011 | Contant et al. |
| 2013/0144652 A1* | 6/2013 | Roberson ............ G06F 19/3431 705/3 |
| 2013/0297536 A1 | 11/2013 | Almosni et al. |
| 2014/0032234 A1 | 1/2014 | Anderson |
| 2014/0114680 A1 | 4/2014 | Mills et al. |
| 2014/0236623 A1* | 8/2014 | Shiovitz ................ G06Q 50/24 705/2 |
| 2015/0324541 A1 | 11/2015 | Cheung et al. |
| 2016/0113569 A1 | 4/2016 | Zhao et al. |

(Continued)

OTHER PUBLICATIONS

Sánchez E (2006). What effects do mobile phones have on people's health? Copenhagen, WHO Regional Office for Europe (Health Evidence Network report; http://www.euro.who.int/document/e89486.pdf, accessed [Feb. 1, 2019]).*

(Continued)

*Primary Examiner* — Mark Holcomb
(74) *Attorney, Agent, or Firm* — Christopher M. Pignato (57) ABSTRACT

Embodiments of the present invention provide methods, computer program products, and a system for determining and providing health risk alerts. Embodiments of the present invention can be used to collect numbers entered by a user, which in turn are used to determine the health risks of the behavior of the user. Embodiments of the present invention can be used to issue alerts to a person of interest based, at least in part, on the number strings entered by the user.

1 Claim, 4 Drawing Sheets

(56) References Cited

U.S. PATENT DOCUMENTS

2016/0262681 A1 9/2016 Patterson et al.
2016/0361032 A1 12/2016 Carter et al.
2017/0086727 A1 3/2017 Dagum

OTHER PUBLICATIONS

Frias-Martinez et al., "Forecasting Socioeconomic Trends With Cell Phone Records", DEV '13 Jan. 11-12, 2013, Bangalore India, © 2013, ACM 978-1-4503-1856-3/13/01, 10 pages.
Martinez-Moncada, Diego, "Lucky & Unlucky Numbers Around the World", Daily Infographic, Aug. 27, 2012, 6 pages, <http://www.dailyinfographic.com/lucky-unlucky-numbers-around-the-world-infographic>.
Wiegand, Douglas M., PhD., "Evaluation of Job Stress and Work-related Health Concerns at a Telephone Call Center", HE | Health Hazard Evaluation Program, U.S. Department of Health and Human Services | Centers for Disease Control and Prevention | National Institute for Occupational Safety and Health, Report No. 2012-0211-3197, Nov. 2013, 22 pages.
"Emergency telephone number", From Wikipedia, the free encyclopedia, This page was last edited on May 1, 2017, 6 pages, <https://en.wikipedia.org/wiki/Emergency_telephone_number>.
"IP address", From Wikipedia, the free encyclopedia, This page was last edited on Apr. 14, 2017, 10 pages, <https://en.wikipedia.org/wiki/IP_address>.
Arffa et al., "Health Trend Identification", U.S. Appl. No. 15/715,353, filed Sep. 26, 2017, 25 pages.
Appendix P—List of IBM Patents or Patent Applications Treated as Related, Filed herewith, 2 Pages.

* cited by examiner

HEALTH TREND IDENTIFICATION

BACKGROUND

The present invention relates generally to the field of health monitoring, and more particularly to health risk notifications.

People use a set of numbers every day in business, lifestyle, reference, and identification. Commonly used sets of numbers include phone numbers, driver's license numbers, credit card numbers, flight numbers, IP addresses, zip codes, and vital sign numbers. These sets of numbers generally follow a pattern when they are assigned to a person or organization. For instance, some sets of numbers are reserved as a special designation or service, such as "911", which is reserved for emergency services. Phone number area codes and zip codes are sets of numbers designated to a localized area, e.g., a zip code of "77XXX" is a Texas prefix, and the area code of "281- . . . " is a Houston area prefix. Prefixes such as "1-800- . . . ", "1-877- . . . ", and "1-888- . . . " for a phone number designate that the set of numbers is a toll-free phone number. Outside of designation and regulations of a set of numbers, some people or entities can request a set of numbers, which can hold symbolic meaning to the owner. In some cases, a number can hold cultural, spiritual, or even superstitious connotations. For example, in regions of North America, the number "7" is generally held as a lucky number, but the number "13" is viewed as an unlucky number; even to extremes where sometimes aircraft seat rows and buildings will lack a thirteenth row or floor due to consumer avoidance of the number.

SUMMARY

Embodiments of the present invention disclose a method, a computer program product, and a system for determining and providing health risk alerts. In one embodiment of the present invention, a method is provided comprising: collecting a set of sequence of numbers comprising one or more digits accessed by a user; determining a frequency for each of the one or more digits in the set of sequence of numbers; determining a set of categories for each of the one or more digits based, at least in part, on an associated utility for the sequence of numbers; determining that the frequency of at least one of the one or more digits exceeds a health risk threshold value; and, responsive to determining that the frequency of at least one of the one or more digits exceeds the health risk threshold value, determining a set of health risks associated with the one or more digits.

DETAILED DESCRIPTION

Embodiments of the present invention recognize that users interact with a set of numbers on a daily basis. For example, commonly used sets of numbers include phone numbers, driver's license numbers, credit card numbers, flight numbers, IP addresses, zip codes, and vital sign numbers. Often, it is difficult to discern meaningful patterns from these set of numbers. Embodiments of the present invention provide solutions for discerning meaningful patterns from these set of numbers. For example, embodiments of the present invention can identify health risks from the use of numbers in everyday activities. As described in greater detail later in the specification, embodiments of the present invention provide the capability to collect one or more number strings, analyze a frequency of a digit over a rolling window of time, determine a set of health risks, and alert a person of interest. As used herein, a person of interest can be, but is not limited to, a user (i.e., the person attributed to the input of a set of numbers), a doctor monitoring the behavior of a patient, some healthcare authority, or any other person having the permission of the user.

Figure 1:
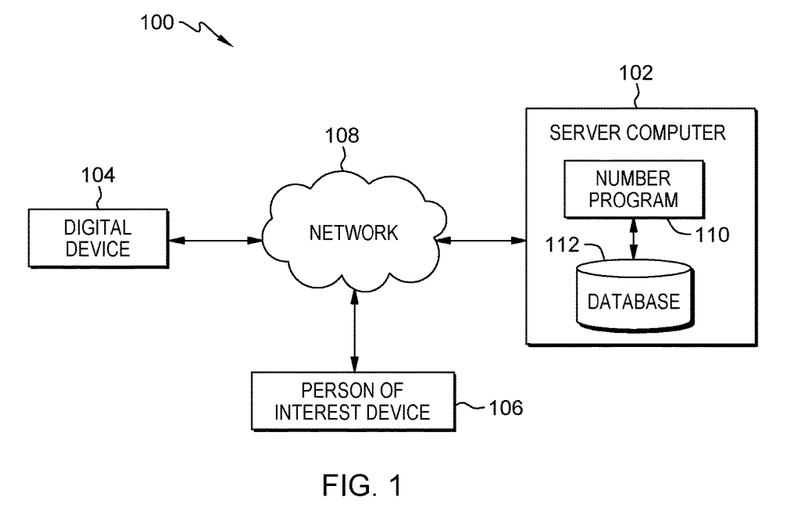
FIG. 1 is a functional block diagram illustrating a number collection environment, in accordance with an embodiment of the present invention.

FIG. 1 is a functional block diagram illustrating a number collection environment, generally designated 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims. Implementation of embodiments of the invention may take a variety of forms, and exemplary implementation details are discussed subsequently with reference to the Figures.

Number collection environment 100 includes server computer 102, digital device 104, and person of interest device 106, all interconnected over network 108. Network 108 can be, for example, a telecommunications network, a local area network (LAN), a wide area network (WAN), such as the Internet, or a combination of the three, and can include wired, wireless, or fiber optic connections. Network 108 can include one or more wired and/or wireless networks that are capable of receiving and transmitting data, voice, and/or video signals, including multimedia signals that include voice, data, and video information. In general, network 108 can be any combination of connections and protocols that will support communications among server computer 102, digital device 104, person of interest device 106, and other computing devices (not shown) within number collection environment 100.

Digital device 104 and person of interest device 106 can each be a laptop computer, a tablet computer, a smart phone, other mobile computing device, wearable computing device, or any programmable electronic device capable of communicating with various components and devices within number collection environment 100, via network 108. In general, digital device 104 and person of interest device 106 each represent any programmable electronic device or combination of programmable electronic devices capable of executing machine readable program instructions and communicating with other computing devices (not shown) within number collection environment 100 via a network, such as network 108. Digital device 104 and person of interest device 106 may include internal and external hardware components, as depicted and described in further detail with respect to FIG. 4. In the embodiments of the present invention, digital device 104 is any digital device capable of connecting to network 108 that a user uses to input a set of numbers, wherein the set of numbers can be, but not limited to, a phone number, a personal identification number, a band card, an IP address, or fitness data. Person of interest device 106 is any device connected to network 108 that can receive alarms or notifications from number program 110, wherein a person of interest can be, but is not limited to, the user, a guardian or caretaker of the user, a personal physician to the user, or an emergency service authority (e.g., "911").

Server computer 102 can be a standalone computing device, a management server, a web server, a mobile computing device, or any other electronic device or computing system capable of receiving, sending, and processing data. In other embodiments, server computer 102 can represent a server computing system utilizing multiple computers as a server system, such as in a cloud computing environment. In another embodiment, server computer 102 can be a laptop computer, a tablet computer, a netbook computer, a personal computer (PC), a desktop computer, a personal digital assistant (PDA), a smart phone, or any other programmable electronic device capable of communicating with digital device 104, person of interest device 106, and other computing devices (not shown) within number collection environment 100 via network 108. In another embodiment, server computer 102 represents a computing system utilizing clustered computers and components (e.g., database server computers, application server computers, etc.) that act as a single pool of seamless resources when accessed within number collection environment 100.

In other embodiments, server computer 102 and digital device 104 are a single device. In other embodiments, server computer 102 and person of interest device 106 are a single device. In other embodiments, server computer 102, digital device 104, and person of interest device 106 are a single device. Server computer 102 includes number program 110 and database 112. Server computer 102 may include internal and external hardware components, as depicted and described in further detail with respect to FIG. 4.

Number program 110 is a program capable of determining and providing health risk alerts associated with a user based, at least in part, on one or more number strings collected from the user. In one embodiment, number program 110 collects from a user, via digital device 104, one or more numbers strings each time a user utilizes the one or more number strings using digital device 104, and determines a set of health risks based on part on a frequency of use of a digit in the one or more number strings over a rolling window of time. A "number string", as used herein, refers to a series of one or more digits arranged in a particular order that acts as an identifier. For example, number string can be, but is not limited to, a phone number, a credit card number, or an internet protocol (IP) address. As used herein, a "number string" can be used interchangeably with a sequence of numbers. In one embodiment, number program 110 may be an application, downloaded from an application store or third party provider, capable of being used in conjunction with an existing health monitoring system, such as a fitness tracker or a vital signs monitor. In one embodiment, number program 110 stores the one or more number strings on database 112. In one embodiment, number program 110 acquires medical documentation from database 112. In another embodiment, number program 110 acquires a set of medical history of the user. Number program 110 is depicted and described in further detail with respect to FIG. 2.

Database 112 is a repository for data used by number program 110. Database 112 can be implemented with any type of storage device capable of storing data and configuration files that can be accessed and utilized by server computer 102, such as a database server, a hard disk drive, or a flash memory. Database 112 stores one or more numbers strings that number program 110 collects from a user over a rolling window of time. Database 112 stores a library of number strings. A library of number strings contains one or more number strings corresponding to a utility that number program 110 gathered from network 108. A utility, as used herein, is an end function that a number string connects to, such as a business or service. For example, a number string can connect to a utility such as restaurants, customer service hotlines, or online shopping websites.

Database 112 stores medical documentation that correlate categories to a set of health risks. Database 112 stores a set of medical history of the user, wherein the medical history contains health status of the user, such as age, height, weight, existing conditions (e.g. obesity, high cholesterol, depression, etc.), and pre-existing conditions. The set of medical history also contains a list of concerns that are to be avoided by the user based, at least in part, upon the set of medical history of the user. For example, for a user with a medical history of dietary problems, the list of concerns can include foods with high cholesterol, high calories, high sugar, and high fat.

Figure 2:
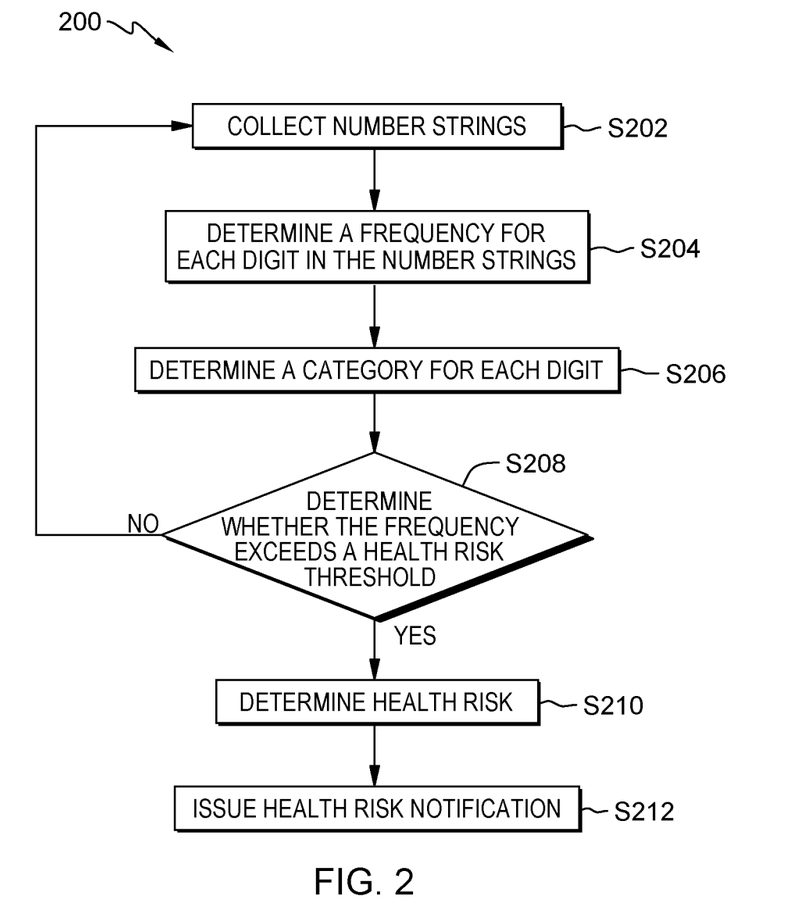
FIG. 2 is a flowchart depicting operational steps of a number program, on a server computer within the number collection environment of FIG. 1, for alerting users to health risks, in accordance with an embodiment of the present invention.

FIG. 2 is a flowchart 200 depicting operational steps of number program 110, on server computer 102 within number collection environment 100 of FIG. 1, for alerting users to health risks, in accordance with an embodiment of the present invention.

Number program 110 collects one or more number strings (S202). In this embodiment, number program 110 collects one or more number strings that a user utilizes in daily activities on digital device 104 by monitoring call logs of the user. Number program 110 can then store the one or more collected number strings on database 112. For example, in this embodiment, number program 110 collects phone numbers the user calls by monitoring call logs of digital device 104, and stores the phone numbers and associated metadata (e.g., call timestamp) to database 112 each time the user places a call on digital device 104. In another embodiment, number program 110 collects credit card number entries by monitoring credit card numbers the user enters onto digital device 104, and stores the credit card number and associated metadata to database 112 each time the user performs a business transaction. In another embodiment, number program 110 collects IP addresses by monitoring the IP addresses the user accesses on digital device 104, and stores the IP addresses and associated metadata to database 112.

Number program 110 determines a frequency for each of one or more digits in the one or more number strings (S204). In this embodiment, number program 110 determines a frequency of each of the one or more digits by counting the occurrence of each of the one or more digits in the one or more number strings (collected in operation S202). Number program 110 determines the frequency of each of the one or more digits in the one or more number strings by evaluating the one or more number strings that fall within a rolling window of time. A rolling window of time is a preconfigured metric of time measured from a present date to a past date, and can be, but is not limited to, any combination of days, weeks, months, or years. For example, if the rolling window is preconfigured to 30 days, then number program 110 only evaluates one or more number strings that were collected from present day to 30 days prior to present day. In another example, the rolling window can be seven days. In the same example, number program 110 can then collect the number string "123-888-8888" once on Monday, once on Wednesday, and once on Friday of a first week. Number program 110 can determine the frequency for each of the one or more digits of the number string during the rolling window of time of seven days as: three for digit "1", three for digit "2", three for digit "3", and twenty-one for digit "8". If number program 110 collects no number strings by the end of Wednesday of a second week, then number program 110 determines the frequency for each digit over the rolling window of time of seven days as: one for digit "1", one for digit "2", one for digit "3", and seven for digit "8", since only the prior Friday of the first week falls within the rolling window of time of seven days.

Number program 110 determines a category for each of one or more digits (S206). In this embodiment, number program 110 determines a set of categories (i.e., a common characteristic shared by each of the one or more digits of the one or more number strings) for each of the one or more digits by identifying a set of characteristics for each of the one or more digits, and associating the set of characteristics to a corresponding set of categories. The set of characteristics can include, but not limited to, numerical patterns that appear in each of the one or more number strings, a mode of entry for each of the one or more number strings, and a utility for the use of each of the one or more number strings.

A numerical pattern, as used herein, refers to a characteristic related to the composition and sequence of numbers in the number string. The numerical pattern can be, but is not limited to, a string length, or a number string prefix or suffix (e.g., area codes, zip codes, bank routing numbers, etc.), wherein the prefix and suffix can be referenced by number program 110 by using the library of number strings on database 112. For example, number program 110 identifies that a number string "713-333-4444" is composed of ten numbers and has a prefix of "713". Number program 110 determines the set of categories as "Ten number string" and "Houston area code (713)", and associates both categories to digits "7", "1", "3", and "4" as a single use of the number string. In another example, the user places phone calls with prefixes "1-800", "1-888", "1-877", and "1-855" using digital device 104. Number program 110 determines that the one or more number strings have prefixes of "1-800", "1-888", "1-877", and "1-855", which number program 110 determines these prefixes as customer service number strings by referencing the prefixes to the library of number strings located on database 112. Number program 110 determines a "customer service" category, and assigns the "customer service" category to the digits contained in the number strings containing the prefixes "1-800", "1-888", "1-877", and "1-855" for each use of the customer service number string.

A mode of entry, as used herein, refers to a characteristic that conveys how the number string is entered into digital device 104 by a user. The mode of entry can be a type of device used for digital device 104. For example, a user enters the number string "713-333-4444" to place a phone call on a mobile phone of the user. Number program 110 identifies that the number string was entered using the mobile phone of the user, determines a "mobile phone" category, and assigns the "mobile phone" category to digits "7", "1", "3", and "4" as a single use of the number string.

In a further embodiment, mode of entry is a characteristic related to a context of how the number string is entered into digital device 104 by a user, wherein the context is an operation or function that digital device 104 performs as a result of the entry of a number string. For example, after the user enters the number string "713-333-4444" onto their mobile phone, the user enters onto their mobile phone that the number string is being used to place a phone call (i.e., the places the call using the number string). Number program 110 identifies that the number string was entered to place a phone call using the mobile phone, determines a "phone call" category, and assigns the "phone call" category to digits "7", "1", "3", and "4" as a single use of the number string. In another example, a user uses a personal computer as a digital device 104 to visit a website. When the user selects the website (i.e., the user clicks on a website link or enters a website domain name to access the website), the computer of the user accesses the website using an IP address "77.11.33.44" (a number string). Number program 110 identifies that the IP address number string was used to access a website, determines a "web browsing" category, and assigns the "web browsing" category to digits "7", "1", "3", and "4" as a single use of the number string. In another example, a user uses a personal computer as a digital device 104 to make a purchase on a website. The user is prompted to enter purchasing credentials (i.e., credit card number, expiration date, security code, etc.). The user enters their purchasing credentials and places a purchase order. Number program 110 identifies that the purchasing credentials entered by the user is being used to make a purchase, determines an "online shopping" category, and assigns "online shopping" category to the digits composing of the purchasing credentials as a single use of the purchasing credential number string.

A utility, as used herein, refers to a characteristic related to a function, business type, or service that a number string is addressed or is associated with, and is defined by the library of number strings contained on database 112. For example, a user enters the number string "713-333-4444" using digital device 104. Number program 110 references the number string to the library of number strings and determines the number string is for a restaurant. Number program 110 determines a "restaurant" category, and assigns "restaurant" category to the digits "7", "1", "3", and "4" as a single use of the number string.

Number program 110 determines whether the frequency of at least one of the one or more digits exceeds a health risk threshold value (S208). In this embodiment, number program 110 determines whether the frequency of at least one of the one or more digits exceeds a health risk threshold value by continuously monitoring the frequency of the one or more digits collected over a rolling window of time, and checking the frequency against a corresponding health risk threshold value assigned to each of the one or more digits, wherein the health risk threshold value is a numerical value determined by average user trends for each of the one or more digits for accessing one or more number strings. Where number program 110 determines that the frequency of at least one or more digits over the rolling window of time exceeds the corresponding health risk threshold value, number program 110 determines a health risk (S210). Where number program 110 determines that the frequency of at least one or more digits over the rolling window of time does not exceed the health risk threshold value, number program 110 continues to collect one or more number strings from digital device 104 (e.g., S202). For example, if the health risk threshold value is determined to be 100 for digit "8" for a rolling window of time of 30 days, and number program 110 determines that the frequency is 101 or greater for digit "8", then number program 110 determines a health risk. If number program 110 determines that the frequency is 100 or less, number program 110 continues to collect one or more number strings from digital device 104.

Responsive to determining that a frequency of at least one or more digits exceeds a corresponding health risk threshold value, number program 110 determines a set of health risks (S210). In this embodiment, number program 110 determines a set of health risks by selecting a set of top categories corresponding to each of one or more digits, acquiring a set of medical documentation corresponding to the set of top categories, determining a set of health risks corresponding to the set of top categories, and selecting the set of health risks corresponding to the set of top categories as described in greater detail with regard to FIG. 3, flowchart 300.

Responsive to determining that the frequency of at least one or more digits over the rolling window of time does not exceed a corresponding health risk threshold value, number program 110 continues to collect one or more number strings from digital device 104 (S202).

Number program 110 issues a health risk notification to a person of interest (S212). In this embodiment, number program 110 issues a health risk notification to a person of interest by sending the health risk notification to person of interest device 106, thus notifying a person of interest that the behavior of the user is hazardous to the health of the user. For example, a health risk notification can be in the form of an email on a computer of a doctor or healthcare professional monitoring the user, a text message on a mobile phone of the user, or a phone call to emergency services. In one embodiment, number program 110 issues a health risk notification report to a person of interest detailing the set of health risks and behaviors of the user that triggered the health risk notification. For example, number program 110 issues a health risk notification detailing that the user has been working late by accessing work related computers, calling restaurants and eating unhealthy takeout food, and has an alarm to wake up early the next day. Additionally, number program 110 details the set of health risks found on medical documentation that working late and waking up early equates to lack of sleep, which is found to be a health concern; and that frequent consumption of restaurant food equates to high consumption of sodium, sugars, and fats, which is found to be a health concern.

In another embodiment, number program 110 can generate an interactive user interactive interface that displays a health risk report that includes the health risk notification. For example, number program 110 can generate an interactive user interface that includes one or more input fields (e.g., selectable fields, drop down menus, input boxes, etc. denoted by one or more icons or graphical elements) that can modify the health report shown. In this other embodiment, the health report shown can include the identified set of health risks and the top categories that affect the user. In other embodiments, the health report can include a corresponding graph that illustrates the health risks of the user and various mitigating actions (i.e., options) the user can take to decrease those health risks. The user can then interact with the user interface to modify the health report. For example, the interface display can contain an input field that increases or decreases an amount of exercise performed by the user. Responsive to a user selection to increase the amount of exercise performed by the user, the interactive display can show a decrease in the health risks the user is exposed to. In another embodiment, number program 110 can include in the generated health report, mitigating actions the user currently takes (e.g., level of health, diet, etc.).

Figure 3:
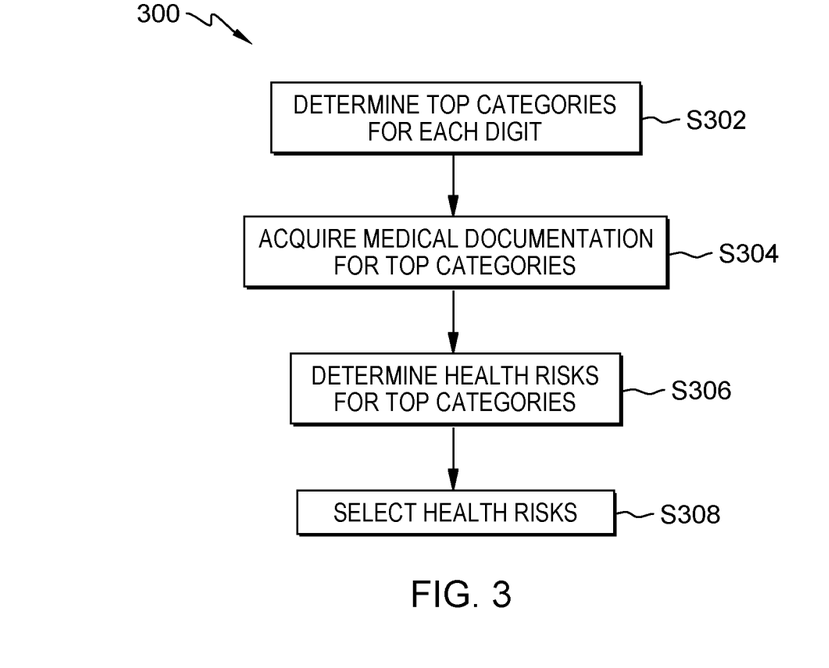
FIG. 3 is a flowchart depicting operational steps of determining a set of health risks process, on a server computer within the number collection environment of FIG. 1, in accordance with an embodiment of the present invention.

FIG. 3 is a flowchart 300 depicting operational steps of determining a set of health risks process, on a server computer within the number collection environment 100 of FIG. 1, in accordance with an embodiment of the present invention.

Number program 110 determines a set of top categories for each of the one or more digits (S302). In this embodiment, number program 110 determines a set of top categories corresponding to each of the one or more digits by selecting the category from the set of categories having a greater frequency of use for the digit in comparison to the other determined categories associated with the digit over the rolling window of time. For example, number program 110 determines that digit "8" corresponds to restaurants, customer service hotlines, and online shopping websites categories, where the restaurant category has a frequency of ten counts of "8", the customer service hotline category has a frequency of three counts of "8", and the online shopping website category has a frequency of one count of "8". Number program 110 determines the restaurant category was accessed the most frequent, and selects the restaurant as the top category for digit "8".

Number program 110 acquires a set of medical documentation corresponding to a set of top categories (S304). In this embodiment, number program 110 acquires a set of medical documentation corresponding to a set of top categories by retrieving the set of medical documentation from database 112, wherein the set of medical documentation contains a description of any health risks that are related to the corresponding top categories. For example, number program 110 determines that a set of top categories are restaurants, alarm settings, and work. Number program 110 acquires a set of medical documentation regarding frequent restaurant dining, sleeping patterns (e.g., too much, too little, intermittent, or unusual sleeping patterns), and excessive work. In one embodiment, number program 110 acquires a set of medical documentation from a medical library or medical research publication database. In another embodiment, number program 110 acquires a set of medical documentation by a category search on the Internet.

Number program 110 determines a set of health risks corresponding to a set of top categories (S306). In this embodiment, number program 110 determines a set of health risks corresponding to a set of top categories by obtaining a set of health risks from the set of medical documentation that details a set of health risks and matching the set of health risks to a corresponding top category. For example, number program 110 obtains from the set of medical documentation that frequent restaurant habits include health risks such as: high calorie diet, large portions, high sodium, high sugar, and high fat. For poor sleeping habits, the set of medical documentation correlate health risks such as: poor immunity, obesity, poor mental wellbeing, and diabetes. For excessive work, the set of medical documentation correlate health risks such as: poor sleeping habits, poor mental wellbeing, fatigue, cardiovascular disorders, gastrointestinal disorders, and high chance of accidents.

Number program 110 selects the set of health risks (S308). In this embodiment, number program 110 selects the set of health risks by selecting the set of health risks obtained from the set of medical documentation that correlates to a set of top categories (determined in operation S306). For example, number program 110 selects the set of health risks that correspond to the set of top categories of frequent restaurant habits, poor sleeping, and excessive work, which number program 110 determined the set of health risks from the set of medical documentation to be high calorie diet, large portions, high sodium, high sugar, high fat, poor immunity, obesity, poor mental wellbeing, diabetes, poor sleeping habits, fatigue, cardiovascular disorders, gastrointestinal disorders, and high chance of accidents.

In a further embodiment, number program 110 selects only a set of health risks that match a list of concerns based, at least in part, on a set of medical history of the user by acquiring the list of concerns of the user from database 112, and selecting the set of health risks that match the list of concerns. For example, a user has a medical history of obesity, and correspondingly has a list of concerns related to obesity (e.g., high calorie diet, large portions, and high fat) located on database 112. If number program 110 determines the top categories for the user are frequent restaurant habits, poor sleeping, and excessive work, then number program 110 acquires from medical documentation the corresponding health risks to the top categories (e.g., high calorie diet, large portions, high sodium, high sugar, high fat, poor immunity, obesity, poor mental wellbeing, diabetes, poor sleeping habits, fatigue, cardiovascular disorders, gastrointestinal disorders, and high chance of accidents), acquires the list of concerns from database 112, and selects the set of health risks that match between the set of health risks obtained from medical documentation and the list of concerns (i.e., number program 110 selects high calorie diet, large portions, and high fat as the set of health risks)

Figure 4:
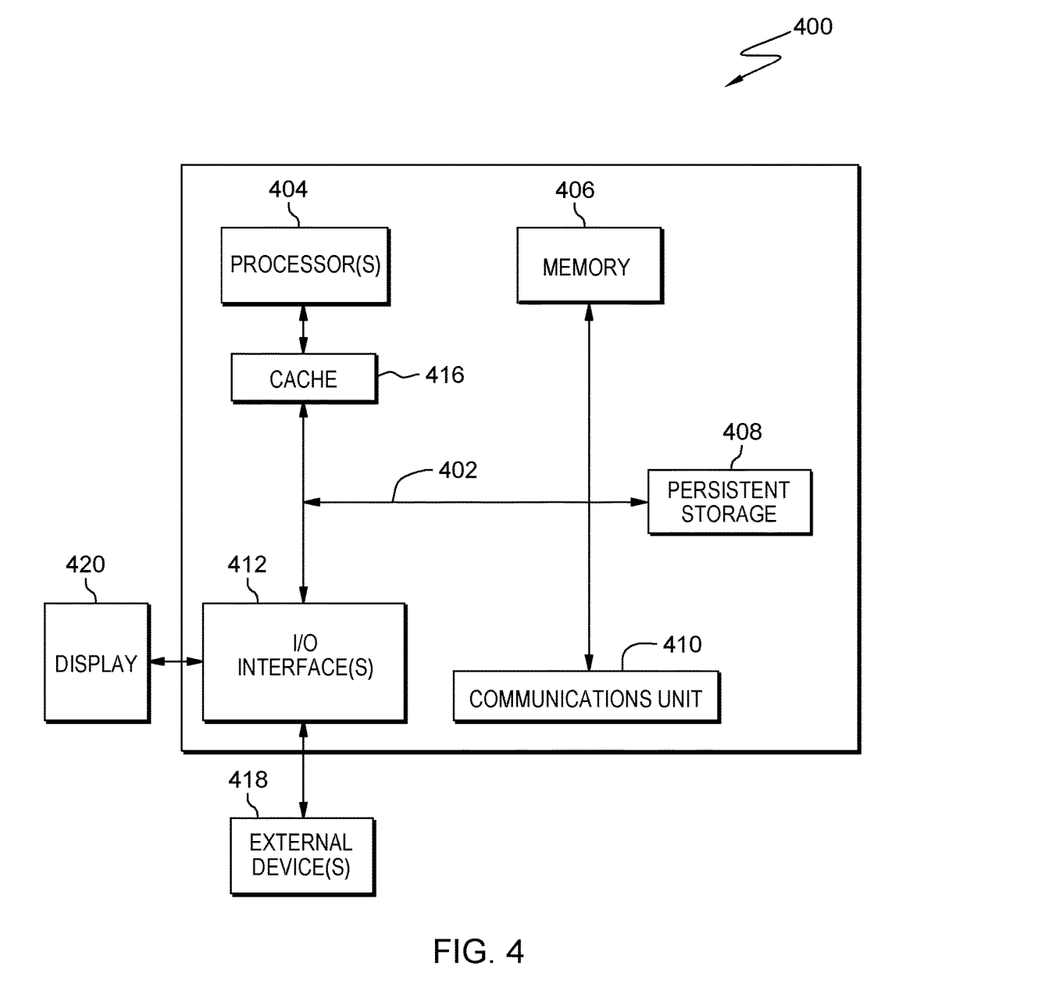
FIG. 4 depicts a block diagram of components of the server computer executing the intelligent mapping program within the distributed data processing environment of FIG. 1, in accordance with an embodiment of the present invention.

FIG. 4 depicts a block diagram of components of computer system 400, which is representative of the computer systems of within number collection environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Server computer 102 includes communications fabric 402, which provides communications between cache 416, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a crossbar switch.

Memory 406 and persistent storage 408 are computer readable storage media. In this embodiment, memory 406 includes random access memory (RAM). In general, memory 406 can include any suitable volatile or non-volatile computer readable storage media. Cache 416 is a fast memory that enhances the performance of computer processor(s) 404 by holding recently accessed data, and data near accessed data, from memory 406.

Number program 110 may be stored in persistent storage 408 and in memory 406 for execution by one or more of the respective computer processors 404 via cache 416. In an embodiment, persistent storage 408 includes a magnetic hard disk drive. Alternatively, or in addition to a magnetic hard disk drive, persistent storage 408 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices. In these examples, communications unit 410 includes one or more network interface cards. Communications unit 410 may provide communications through the use of either or both physical and wireless communications links. Number program 110 may be downloaded to persistent storage 408 through communications unit 410.

I/O interface(s) 412 allows for input and output of data with other devices that may be connected to server computer 102. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., Number program 110, can be stored on such portable computer readable storage media and can be loaded onto persistent storage 408 via I/O interface(s) 412. I/O interface(s) 412 also connect to a display 420.

Display 420 provides a mechanism to display data to a user and may be, for example, a computer monitor.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method performed on a processor executing method steps comprising:
   collecting a set of sequence of numbers comprising one or more digits accessed by a user;
   determining a frequency for each of the one or more digits in the set of sequence of numbers;
   determining a set of categories for each of the one or more digits based on either an associated utility for the sequence of numbers or a mode of entry for the sequence of numbers;
   determining that the frequency of at least one of the one or more digits exceeds a threshold value, wherein the threshold value serves as a trigger to identify a first subset of categories from the determined set of categories associated with each of the one or more digits;
   responsive to determining that the frequency of at least one of the one or more digits exceeds a threshold value, identifying a set of health risks associated with the first subset of categories of the determined set of categories associated with each of the one or more digits wherein identifying a set of health risks associated with the first subset of categories comprises:

determining the first subset of categories from the determined set of categories associated with a digit of a sequence of numbers of the set of sequence of numbers having a greater frequency of use for the digit of the first sequence of numbers in comparison to a second subset of categories associated with the digit of the sequence of numbers;

linking a respective behavior to the first subset based on either an associated utility for the sequence of numbers or a mode of entry for the sequence of numbers;

accessing a set of medical documentation that detail a set of health risks and a set of behaviors that cause each health risk in the set of health risks;

matching the respective linked behavior to a behavior specified in the set of medical documentation; and identifying a set of health risks from the set of medical documentation that matches the respective linked behavior;

generating, a health risk notification that includes a health risk report based on the identified set of health risks;

issuing the generated health risk notification to a person of interest based, at least in part, on the identified set of health risks;

generating a user interactive interface that displays the issued health risk notification, wherein the generated user interactive interface includes one or more graphical icons and selectable fields that can modify the health risk report;

receiving, one or more user selected options from the generated user interactive display; and responsive to receiving the one or more user selected options from the generated user interactive display, modifying the health risk report to increase or decrease a health risk based on the received one or more user selected options.

\* \* \* \* \*